(12) United States Patent
Meij et al.

(10) Patent No.: US 6,245,829 B1
(45) Date of Patent: Jun. 12, 2001

(54) RADIATION-CURABLE COMPOSITION

(75) Inventors: Theodoor H. Meij; Marten Houweling, both of Zwolle; Aylvin J. A. A. Dias, Maastricht; Johan F. G. A. Jansen, Geleen; Rudolfus A. T. M. Van Benthem, Sittard, all of (NL)

(73) Assignee: DSM NV, Heerlen (NL)

( * ) Notice: Subject to any disclaimer, the term of this patent is extended or adjusted under 35 U.S.C. 154(b) by 0 days.

(21) Appl. No.: 09/362,900

(22) Filed: Jul. 29, 1999

(30) Foreign Application Priority Data

Jan. 30, 1997 (NL) .................................... 1005129
Jan. 20, 1998 (WO) .................... PCT/NL98/00035

(51) Int. Cl.⁷ ............................. C08F 2/46; C08F 20/56; C08F 120/56; C08F 20/58; C08F 120/58
(52) U.S. Cl. ................... 522/175; 522/173; 560/205; 560/215
(58) Field of Search .................... 522/173, 175; 560/215, 205

(56) References Cited

U.S. PATENT DOCUMENTS

| | | |
|---|---|---|
| 3,366,613 | 1/1968 | Kelley . |
| 4,016,192 * | 4/1977 | Tomalia et al. . |
| 4,910,268 * | 3/1990 | Kobayashi . |
| 5,225,480 | 7/1993 | Tseng et al. . |
| 5,350,631 | 9/1994 | Tseng et al. . |
| 5,354,827 | 10/1994 | Muller et al. . |
| 5,360,836 | 11/1994 | Chevallier et al. . |
| 5,629,359 | 5/1997 | Peeters et al. . |

FOREIGN PATENT DOCUMENTS

| | | |
|---|---|---|
| 0263749 A1 | 4/1988 | (EP) . |
| 0448399 A2 | 9/1991 | (EP) . |
| 0499923 A1 | 8/1992 | (EP) . |
| 0685535 A1 | 12/1995 | (EP) . |

* cited by examiner

*Primary Examiner*—Susan W. Berman
(74) *Attorney, Agent, or Firm*—Pillsbury Winthrop LLP

(57) ABSTRACT

The invention relates to a radiation curable composition comprising a mono or mulit valent carboxylic ester of a β-hydroxyalkylamide group containing compound, in which the carboxylic ester is derived from an α,β-ethylenically unsaturated carboxylic acid. A coating composition based on this composition has a high rate of polymerisation and shows the desired chemical and mechanical properties.

5 Claims, No Drawings

RADIATION-CURABLE COMPOSITION

The invention relates to a radiation-curable composition.

During radiation curing processes the transformation of the fluid applied film to a solid crosslinked network can be considered to progress through three distinct stages being induction, polymerisation and attainment of maximum cure plateau. (Chemistry and Technology of UV and EB formulations, Volume IV, Oldring, 1991, pages 8–12).

Factors which improve or inhibit cure rate are, for example, the lamp system (UV-dose, intensity, wavelength, IR-content) and the chemical system (reactivity, absorption, coating weight, pigmentation, temperature, oxygen inhibition and substrate).

For commercial coating operations, it is necessary that the coating achieves a tackfree surface within seconds or less, because the interval between application of the coating and stacking or rewinding of the coated substrate is very short. Failure of the coating to achieve a non-tacky surface in this brief interval will result in the layers of coated substrate (in a stack or roll) sticking together ("blocking").

It is the object of the present invention to provide a coating composition having a high cure rate or rate of polymerisation and having the desired chemical and mechanical properies.

The radiation curable composition according to the invention comprises a mono or multi valent carboxylic ester of a β-hydroxyalkylamide group containing compound, in which the carboxylic ester is derived from an α,β-ethylenically unsaturated carboxylic acid.

The composition according to the invention results in high maximum polymerization rates.

According to a preferred embodiment of the invention the compound is according to formula (I):

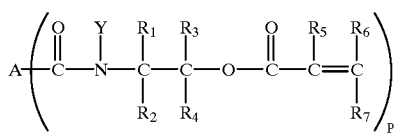

(I)

where:
A=hydrogen, or a monovalent or polyvalent organic group which is derived from a saturated or an unsaturated ($C_1$–$C_{60}$) alkyl group, or derived from an ($C_6$–$C_{10}$) aryl group,
Y=hydrogen, an ($C_1$–$C_8$) alkyl group or

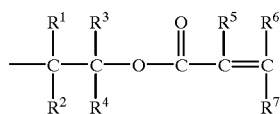

(II)

$R^1$, $R^2$, $R^3$, $R^4$ are, identical or different, hydrogen or a linear, branched or cyclic ($C_1$–$C_8$) alkyl chain,
$R^5$=hydrogen, ($C_1$–$C_5$)alkyl, —$CH_2OH$ or $CH_2COOX$,
$R^6$, $R^7$=hydrogen, ($C_1$–$C_8$) alkyl, ($C_6$–$C_{10}$)aryl or COOX
X=hydrogen or ($C_1$–$C_8$) alkyl and
p=1 or 2
$R^1$, $R^2$ or $R^3$ may form part of a cycloalkyl group.

The organic groups in A may be substituted with, for example, ethers, esters, hydroxyl, amides, acids, amines or ketones.

Preferably, ester- or hydroxylgroups are applied as substitutents.

Preferably, A is a monovalent organic group which is derived from a saturated ($C_1$–$C_{12}$) alkyl group.

According to another preferred embodiment of the invention A is a polyvalent organic group derived from a saturated ($C_2$–$C_{10}$) alkyl group or a $C_6$-aryl group.

Preferably, Y is hydrogen or methyl.
Preferably, $R^1$, $R^2$, $R^3$ and $R^4$ are hydrogen or methyl.
$R^5$ is preferably hydrogen or (m)ethyl.
$R^6$ and $R^7$ are preferably hydrogen.

The compound applied in the invention generally has a number-average molecular weight (Mn) of between 140 and 2500, and preferably of between 450 and 1000.

The compound can be obtained, for instance, by an esterification reaction between a β-hydroxyalkylamide and an unsaturated carboxylic acid, at a temperature between, for example, 80° C. and 140° C.

Preferably, 1–1.5 mol of acid are used per mole of hydroxide.

Preferably, the reaction takes place in the presence of an organic solvent, such as, for example, xylene, toluene or tetrahydrofuran.

Preferably, the reaction takes place in the presence of a stabilizing compound which prevents polymerization of the unsaturated ester groups under the conditions used for effecting this reaction. The stabilising compound or a mixture of stabilising compounds is generally used in amounts between about 50 and about 2000 ppm and preferably between 75 and 1000 ppm. They can be used in aerobic or anaerobic conditions depending on the stabilising compound.

Suitable stabilizing compounds include, for example, hydroquinone, monomethylhydroquinone, anthraquinone, β-nitrostyrene, phenothiazine and 2,6-di-tert-butyl-4-methyl-phenol (BHT).

The esterification reaction may take place in the presence of a catalyst. Suitable catalysts include strong acids, for example, sulphur-containing organic acids like alkane sulphonic acids and methane sulphonic acid.

Suitable unsaturated carboxylic acids include, for example, (meth)acrylic acid and derivatives, crotonic acid, (semi-ester of) itaconic acid, maleic acid, citaconic acid, mesaconic acid and fumaric acid.

Suitable β-hydroxyalkylamides include, for example, N,N'-bis(di-β-hydroxyethyl)-1,6-hexanediamide, N-di-β-hydroxyethyl acetamide, N,N-bis(di-p-hydroxypropyl)-1,6-hexanediamide, N-di-β-hydroxypropyl acetamide, N-di-β-hydroxyethyl benzamide and N-di-β-hydroxypropyl benzamide. The compound applied in the invention can also be obtained by the reaction between of a β-hydroxyalkyl amide and an unsaturated carboxylic acid chloride, anhydride or ester.

The reaction between the amide and the unsaturated chloride or anhydride preferably takes place at temperature between 0° C. and 30° C. in a solvent in the presence of a base. Suitable solvents include, for example, tetrahydroferan, water, dichloromethane or diethylether. Suitable bases include, for example, pyridine or triethylamine.

Suitable chlorides, anhydrides or esters include the chlorides, anhydrides and esters of the in the foregoing mentioned carboxylic acid.

The reaction between the amide and the unsaturated ester, preferably, takes place at temperatures between 80° C. and 140° C. in the presence of a Lewis acid.

Preferably, an excess of the unsaturated ester is applied. The ester functions both as solvent and as reactant.

Suitable Lewis acids are, for example, tetra alkyl titanate and sulphuric acid.

Another process for the preparation of the compound applied in the invention is the reaction between an oxazoline and an unsaturated carboxylic acid.

Such a reaction can, for example, take place between 50° C. and 140° C.

Suitable oxazolines include, for instance, oxazoline and ($C_1$–$C_{20}$) alkyloxazolines, for instance, ethyl oxazoline and undecyloxazoline.

Suitable unsaturated carboxylic acids include, for example, (meth)acrylic acid and derivatives, crotonic acid, (semi-ester of) itaconic acid, maleic acid, citaconic acid, mesaconic acid and fumaric acid. Preferably, methacrylic acid and acrylic acid are used.

The compound applied in the invention can be cured by means of a free-radical reaction. In these reactions the free radicals can be obtained by radiation initiation.

Radiation-curing preferably takes place by means of, for example, a photochemical process such as, for example, ultraviolet radiation (UV) or a radiation-chemical process such as electron beam (EB).

UV and EB radiation are explained in greater detail by for example Bett et al. in the article entitled "UV and EB curing" (Jocca 1990 (11), pages 446–453).

The amount of the compound according to formule (I) can range between 0.01% by weight and 100% by weight in the composition according to the invention.

Generally, the radiation curable composition according to the invention is substantially solvent free.

The composition according to the invention can be used, for example, in coating compositions, inks and adhesives.

If desired and depending on the application, the compound can be combined with oligomers or polymers which are based, for example, on (meth)acrylate units, maleate units, fumarate units, itaconate units, vinylester units and/or vinylether units.

Due to the relatively high cure speeds the present compounds can also be applied as additives for enhancing the cure speed of a formulation. In general such additives are used in amounts ranging between 0.01% and 25% by weight and preferably in amounts between 0.5% and 10% by weight relatively to the total amount of all ingredients.

After curing the coatings according to the invention have many desired properties such as for example good chemical properties (resistance to solvents, acids, alkalis and moisture), good optical properties and appearance, good mechanical properties (such as hardness, flexibility, adhesion, abrasian resistance, strength and durability), good thermal stability and good weatherability.

The composition comprising the radiation curable binder composition may further comprise pigments, stabilisers and other additives.

The radiation curable formulation generally consists of a prepolymer, a reactive diluent and additives. Two other possible components, depending upon the type of formulation and cure mechanism are pigments and photoinitiator system.

The composition can be applied as a water based coating, as a solvent based coating, as a high solids coating and as a 100% solids coating.

According to a preferred embodiment of the invention the composition is applied as a powder coating.

The ester applied in the present invention can also be used as a crosslinker in powder coating compositions if the compound is composed in such a way that the softening point (glass transition temperature or melting point) is sufficiently high to be used in this application. Generally, this temperature has to be higher than 40° C.

The most preferred irradiation source is ultraviolet light. Ultraviolet light is preferably high intensity light to provide a dosage to achieve reasonable curing rates. In the event that lower energy light is to be applied, it may then be desired to subject the compositions also to elevated temperatures in order to reduce the time for adequate polymerization to occur.

With respect to UV curing equipment we refer to, for example, pages 161–234 of Chemistry and Technology of UV and EB-formulations, Volume 1, Oldring, 1991.

Suitable lamps employed to provide the desired high intensity and availability of wavelength and spectral distribution include for example that available from Fusion Systems, Corp.

A composition according to the present invention can be applied on substrates such as, for example, plastic, paper, board, leather, glass, wood and metal.

This composition is preferably polymerised in the presence of a photoinitiator but it is also possible to polymerise in the absence of a photoinitiator.

Suitable photoinitiators allow for initiation of the curing process with exposure to light having wavelengths between about 200 nm and about 600 nm. Suitable photoinitiators have ketone functionalities and can be aromatic such as, for example, benzophenone. Darocur 1173® (Ciba) is a suitable benzyl-ketal-based photoinitiator, which contains 2-hydroxy-2-methyl-1-phenylpropane-1-one as an active component. Irgacure 184® (Ciba) is an aryl ketone containing hydroxycyclohexyl phenyl ketone as active component, and is a suitable photoinitiator. Irgacure 369® (active component 2-benzyl-2-dimethylaminol-1-(4-morpholinophenyl)-butanone-1) is also suitable. Acyl phosphines, such as for example 2,4,6,-trimethylbenzoyl diphenyl phosphone oxide (Lucerine TPO®, BASF) can also be used, as can Quantacure CPTX® (Octel Chemicals), which contains 1-chloro-4-propoxy thioxanthone as active component. Chemical derivatives of these photoinitiators are suitable, as are mixtures of these photoinitiators. A suitable combination of photoinitiators is Irgacure $_{1800}$∩ (Ciba) consisting of 75% by weight Irgacure 184™ and 25% by weight (bis-(2,6-dimethoxy benzoyl)-2,4,4-trimethylpentyl fosfine oxide). Other suitable photoinitiators can be of the Norrish-II-type, for example, the combinations benzophenone with amine, maleimide with amine, thioxantone with amine and antrachinon with amine.

The invention is explained by reference to the following non-restrictive experiments and examples.

In the following the cure behaviour monitored with "real time infra red spectroscopy". The conversion of the double bonds during the photopolymerisation was monitored by means of infrared (Bruker IFS5S).

Experiment I

Preparation of N-acryloxyethylundecylamide 51.99 g acrylic acid and 0.3 g BHT were heated in a round-bottom flask to 80° C. Under stirring, 81.3 g molten undecyl oxazoline was slowly added during 1 hour maintaining the reaction temperature at 80° C . After stirring for another hour at 80° C. the reaction mixture was poured into 200 ml diethyl ether and washed with water, twice with a 10% sodium bicarbonate solution and twice with water. After drying on magnesium sulfate, filtration and evaporation in vacuo of the solvent 100.5 g of N-acryloxyethylundecylamide was obtained.

EXAMPLE I

Curing of a Mixture Comprising N-acryloxyethylundecylamide 0.99 g of N-acryloxyethylundecylamide according to Experiment I and 0.01 g of Irgacure 184™ were homogenously mixed at room temperature. This mixture was applied as a 10 μm thick film on a gold coated alumina plate.

Subsequently this plate with the film was irradiated in the infrared machine with a dose of 500 mW/cm² and the conversion of the double bonds was monitored:

| maximum rate of polymerization | 35.5 mol kg$^{-1}$s$^{-1}$ |
|---|---|
| time for 90% conversion | 0.3 sec |

Comparative Example A
Curing of a Mixture Comprising Dodecyl Acrylate 0.99 g of dodecyl acrylate and 0.01 g of Irgacure 184™ were homogeneously mixed at room temperature. This mixture was applied as a 10 μm thick film on a gold coated alumina plate.

Subsequently the plate with the film was irradiated in the infrared machine with a dose of 500 mW/cm² and the conversion of the double bonds was monitored;

| maximum rate of polymerization | 1,5 mol kg$^{-1}$s$^{-1}$ |
|---|---|
| time for 90% conversion | 3.32 sec |

Example I and Comparative Example A clearly indicate that the maximum rate of polymerisation of the composition according to the invention is higher.

EXAMPLE II
Curing of a Mixture Comprising 1% N-acryloxyethylundecylamide and Dodecylacrylate 0.01 g of N-acryloxyethylundecylamide according to Experiment I, 0.99 g dodecyl acrylate and 0.01 g of Irgacure 184™ were homogeneously mixed. A 10 μm thick film was put on a gold coated alumina plate.

Subsequently this plate with the film was irradiated in the infrared machine with a dose of 500 mW/cm² and the conversion of the double bonds was monitored:

| maximum rate of polymerization | 1,87 mol kg$^{-1}$s$^{-1}$ |
|---|---|
| time for 90% conversion | 2.59 sec |

EXAMPLE III
Curing of a Mixture Comprising 2% N-acryloxyethylundecylamide and Dodecylacrylate 0.02 g of N-acryloxyethyl-undecylamide according to Experiment I, 0.98 g dodecyl acrylate and 0.01 g of Irgacure 184™ were homogeneously mixed at room temperature. A 10 μm thick film was put on a gold coated alumina plate.

Subsequently this plate with the film was irradiated in the infrared machine in a infrared machine with a dose of 500 mW/cm² and the conversion of the double bonds was monitored.

| maximum rate of polymerization: | 1,96 mol kg$^{-1}$s$^{-1}$ |
|---|---|
| time for 90% conversion: | 2.33 sec |

EXAMPLE IV
Curing of a Mixture Comprising 5% N-acryloxyethylundecylamide and Dodecylacrylate 0.05 g of N-acryloxyethylundecylamide according to Experiment I, 0.95 g dodecyl acrylate and 0.01 g of Irgacure 184™ were mixed. A 10 μm thick film was put on a gold coated alumina plate.

Subsequently this plate with the film was irradiated in the infrared machine with a dose of 500 mW/cm² and the conversion of the double bonds was monitored:

| maximum rate of polymerization | 2,24 mol kg$^{-1}$s$^{-1}$ |
|---|---|
| time for 90% conversion | 2.2 sec |

EXAMPLE V
Curing of a Mixture Comprising 10% N-acryloxyethylundecylamide and Dodecylacrylate 0.10 g of N-acryloxyethylundecylamide according to Experiment I, 0.90 g dodecyl acrylate and 0.01 g of Irgacure 184™ were homogeneously mixed at room temperature.

A 10 μm thick film was put on a gold coated alumina plate. Subsequently this plate with the film was irradiated in the infrared machine with a dose of 500 mW/cm² and the conversion of the double bonds was monitored:

| maximum rate of polymerization | 2,66 mol kg$^{-1}$s$^{-1}$ |
|---|---|
| time for 90% conversion | 1.93 sec |

Experiment II
Preparation of Ethylamide Ethylacrylate

Experiment I was repeated with the exception that instead of undecyloxazoline 2-ethyl-2-oxazoline was applied.
Experiment III
Preparation of N,N-bis(β-hydroxyethyl)acetamide 315 g of diethanolamine were dissolved in 500 g of tetrahydrofuran in a round-bottom flask. Then, 310 g of acetic anhydride were slowly added. The temperature was kept below 5° C. with the aid of a cooling bath. When, after the dropwise addition, exothermic heat was no longer detectable, heating was slowly carried out to 100° C. Tetrahydrofuran and acetic acid were removed under vacuum.
Experiment IV
Preparation of N,N-bis(β-acryloxyethyl)acetamide 100 grams of the product obtained according to Experiment III, 300 grams of toluene, 0.05 gram of hydroquinone monomethyl ether and 147 grams of acrylic acid were combined in a round-bottom flask (1 liter). The solution was azeotropically distilled for 9 hours. After cooling to room temperature, the excess acrylic acid was neutralized with a saturated solution of sodium bicarbonate in water and the pH was adjusted to 12. After separation of the water layer and the toluene layer, the water layer was again extracted with toluene. The combined toluene layers were dried by distilling under vacuum.
Experiment V
Preparation of N,N',N N'-tetrakis(β-acryloxyethyl)-1,6-hexanediamide Experiment IV was repeated with the exception that 320 grams of N,N'-bis(di-β-hydroxyethyl)-1,6-hexanediamide (Primid® XL 552; Rohm & Haas) and 432 grams acid of acrylic acid were mixed in order to obtain N,N',N,N'-tetrakis (β-acryloxyethyl)-1,6-hexanediamide.

EXAMPLE VI
Curing of a Mixture Comprising Ethylamide Ethylacrylate 0.99 g of ethylamide ethylacrylate according to Experiment II and 0.01 g of Irgacure 184™ were homogenously mixed at room temperature. This mixture was applied as a 10 μm thick film on a gold coated alumina plate.

Subsequently this plate with the film was irradiated in the infrared machine with a dose of 500 mW/cm² and the conversion of the double bonds was monitored:

| maximum rate of polymerization | 46.6 mol kg$^{-1}$s$^{-1}$ |
|---|---|
| time for 90% conversion | 0.3 sec |

EXAMPLE VII
Curing of a Mixture Comprising N,N-bis-(β-acryloxyethyl)acetamide 0.99 g of N,N-bis-(β-acryloxyethyl)acetamide according to Experiment IV and 0.01 g of Irgacure 184™ were homogenously mixed at room temperature. This mixture was applied as a 10 μm thick film on a gold coated alumina plate.

Subsequently this plate with the film was irradiated in the infrared machine with a dose of 500 mW/cm² and the conversion of the double bonds was monitored:
maximum rate of polymerization 46.0 mol kg$^{-1}$s$^{-1}$
For the calculations of the rates when molecules with functionalities higher than 1 are used, the molecular weight per acrylate unit is defined as the total molecular weight of the molecule divided by the number of acrylate functionalities.

EXAMPLE VIII
Curing of a Mixture Comprising N,N',N,N'-tetrakis(acryloxyethyl)1,6-hexanediamide 0.99 g of the diamide according to Experiment V and 0.01 g of Irgacure 184™ were homogenously mixed at room temperature. This mixture was applied as a 10 μm thick film on a gold coated alumina plate.

Subsequently this plate with the film was irradiated with a dose of 500 mW/cm² and the conversion of the double in the infrared machine bonds was monitored:
maximum rate of polymerization 45.5 mol kg$^{-1}$s$^{-1}$ The examples VI–VIII show that the acrylate polymerisation is a fast polymerisation which is less dependent on the functionality.

EXAMPLE IX–X
Coating

The compounds according to the Experiments V and VI were mixed with 1.5% by weight of Darocur® 1173 (Ciba Geigy), after which a 50 μm thick film was deposited on glass.

This film was cured with UV light using a medium pressure mercury lamp. The properties of the cured coatings were determined (see Table I).

The pendulum hardness is determined according to König.

The tensile strength is determined according to DIN53504.

The elongation at break is determined according to DIN53504.

TABLE 1

|  | IX | X |
|---|---|---|
| Minimum UV dosage necessary for hard coating in mJ/cm² (IL 390-A light bug) | 600 | 200 |
| UV dosage necessary for | 900 | 600 |

TABLE 1-continued

|  | IX | X |
|---|---|---|
| scourable coating in mJ/cm² (IL 390-A light bug) | | |
| König surface hardness (sec) | 87 | 119 |
| Tensile strength (N/mm²) | 34 ± 1 | 31 ± 1 |
| Elongation at break (%) | 4.0 ± 0.3 | 1.7 ± 0.3 |

Both coatings were found to have a good resistance to water, N-methylpyrolidone, ammonia, detergents, aqueous citric acid solutions and coffee.

Table I shows that coatings according to the invention have good properties after radiation curing. It is possible to obtain films with good combinations of tensile strength and elongation which will result in tough films.

What is claimed is:

1. A radiation curable coating composition comprising a compound according to formula (I).

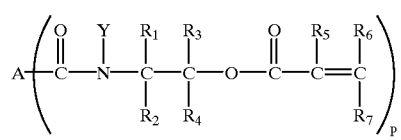

(I)

where:
A=a monovalent or polyvalent organic group selected from saturated or unsaturated (C1–C60) alkyl groups or (C6–C10) aryl groups,
Y=hydrogen, a (C$_1$–C$_8$) alkyl group or

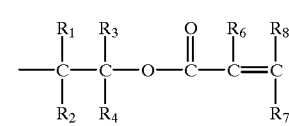

(II)

wherein
R$_1$, R$_2$, R$_3$, R$_4$ are identical or different, hydrogen or a linear, branched or cyclic (C$_1$–C$_8$) alkyl chain,
R$_5$=hydrogen, (C$_1$–C$_5$) alkyl, —CH$_2$OH or CH$_2$COOX,
R$_6$, R,=hydrogen, (C$_1$–C$_8$) alkyl, (C$_6$–C$_{10}$) aryl or coox
X=hydrogen or (C$_1$–C$_8$) alkyl and
p=1 or 2 with the proviso that when p=1,
y=

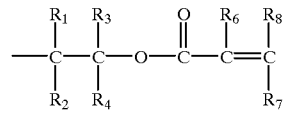

(II)

2. Composition according to claim 1, wherein A is a monovalent organic group selected from saturated (C$_1$–C$_{12}$) alkyl groups or A is a polyvalent organic group selected from saturated (C$_2$–C$_{10}$) alkyl groups of a C$_6$-aryl groups.

3. Composition according to claim 1, wherein Y is hydrogen or methyl, R$_1$, R$_2$, R$_3$, and R$_4$ are hydrogen or methyl, R$_5$ is hydrogen or (m)ethyl and R$_6$, and R$_7$ are hydrogen.

4. Composition according to claim 1, wherein the number average molecular weight of the compound is between 140 and 2500.

5. Coating obtained by radiation curing of a composition according to any one of claims 1–4.

* * * * *